(12) United States Patent
Schwab

(10) Patent No.: US 12,370,004 B2
(45) Date of Patent: *Jul. 29, 2025

(54) DETECTION OF USER TOUCH ON CONTROLLER HANDLE

(71) Applicant: Intuitive Surgical Operations, Inc., Sunnyvale, CA (US)

(72) Inventor: Cedric Schwab, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/404,744

(22) Filed: Jan. 4, 2024

(65) Prior Publication Data

US 2024/0138942 A1 May 2, 2024

Related U.S. Application Data

(63) Continuation of application No. 18/073,329, filed on Dec. 1, 2022, now Pat. No. 11,896,331, which is a
(Continued)

(51) Int. Cl.
*A61B 34/00* (2016.01)
*A61B 34/35* (2016.01)
(Continued)

(52) U.S. Cl.
CPC .............. *A61B 34/35* (2016.02); *A61B 34/74* (2016.02); *A61B 34/76* (2016.02); *B25J 13/025* (2013.01);
(Continued)

(58) Field of Classification Search
CPC ......... A61B 34/35; A61B 34/74; A61B 34/76; A61B 34/25; A61B 90/60; A61B 34/30; B25J 13/025; G06F 3/016
(Continued)

(56) References Cited

U.S. PATENT DOCUMENTS 5,619,180 A 4/1997 Massimino et al.
6,184,868 B1 2/2001 Shahoian et al.
(Continued)

FOREIGN PATENT DOCUMENTS

KR 20100019203 A 2/2010
WO WO-2014149838 A1 9/2014
WO WO-2016114090 A1 7/2016

OTHER PUBLICATIONS

Extended European Search Report for Application No. EP17880592.5 mailed on Jul. 2, 2020, 25 pages.
(Continued)

*Primary Examiner* — Jaime Figueroa
(74) *Attorney, Agent, or Firm* — IP Spring

(57) ABSTRACT

Implementations relate to detecting user touch on a controller handle. In some implementations, a non-controlling mode of a control system is activated, and in the non-controlling mode, one or more actuators are controlled to cause a vibration to be provided on a handle of a controller. The vibration is sensed with one or more sensors, and a difference in the vibration is determined to have occurred relative to a reference vibration using the one or more sensors, where the difference satisfies one or more predetermined thresholds. A controlling mode of the system is activated in response to determining the difference in the vibration, and the vibration is modified on the handle in response to detecting the change in the vibration.

20 Claims, 7 Drawing Sheets

Related U.S. Application Data continuation of application No. 16/470,049, filed as application No. PCT/US2017/066442 on Dec. 14, 2017, now Pat. No. 11,559,364.

(60) Provisional application No. 62/434,990, filed on Dec. 15, 2016.

(51) Int. Cl.
  *B25J 13/02* (2006.01)
  *A61B 90/60* (2016.01)
  *G06F 3/01* (2006.01)

(52) U.S. Cl.
  CPC ............... *A61B 34/25* (2016.02); *A61B 90/60* (2016.02); *G06F 3/016* (2013.01)

(58) Field of Classification Search
  USPC .................................. 700/245–264; 606/130
  See application file for complete search history.

(56) References Cited

U.S. PATENT DOCUMENTS

| | | | |
|---|---|---|---|
| 6,587,750 B2 | 7/2003 | Gerbi et al. | |
| 6,594,552 B1 | 7/2003 | Nowlin et al. | |
| 7,446,752 B2 | 11/2008 | Goldenberg et al. | |
| 7,557,794 B2 | 7/2009 | Rosenberg et al. | |
| 7,746,320 B2* | 6/2010 | Hardwick | A63F 13/285 345/184 |
| 8,016,818 B2 | 9/2011 | Ellis et al. | |
| 8,120,301 B2 | 2/2012 | Goldberg et al. | |
| 8,368,641 B2 | 2/2013 | Tremblay et al. | |
| 8,418,073 B2 | 4/2013 | Mohr et al. | |
| 8,551,002 B2* | 10/2013 | Grant | A61B 5/489 600/459 |
| 8,981,682 B2 | 3/2015 | Delson et al. | |
| 9,283,048 B2 | 3/2016 | Kostrzewski et al. | |
| 9,333,039 B2 | 5/2016 | Kuchenbecker et al. | |
| 9,498,231 B2 | 11/2016 | Haider et al. | |
| 11,132,062 B2 | 9/2021 | Bajaj et al. | |
| 11,166,771 B2 | 11/2021 | Schaible et al. | |
| 11,559,364 B2 | 1/2023 | Schwab | |
| 2006/0290662 A1 | 12/2006 | Houston et al. | |
| 2007/0052496 A1 | 3/2007 | Niemeyer et al. | |
| 2007/0135735 A1* | 6/2007 | Ellis | A61B 90/06 600/587 |
| 2007/0142825 A1* | 6/2007 | Prisco | A61B 34/70 606/1 |
| 2011/0238010 A1* | 9/2011 | Kirschenman | A61M 25/0105 604/95.04 |
| 2012/0026180 A1 | 2/2012 | Kuchenbecker et al. | |
| 2012/0262487 A1 | 10/2012 | Huebner | |
| 2012/0310257 A1* | 12/2012 | Kuchenbecker | A61B 34/76 606/130 |
| 2013/0209980 A1* | 8/2013 | Kuchenbecker | G09B 5/00 434/262 |
| 2014/0018960 A1 | 1/2014 | Itkowitz | |
| 2015/0049036 A1 | 2/2015 | Kim et al. | |
| 2015/0081110 A1 | 3/2015 | Houston et al. | |
| 2016/0081738 A1* | 3/2016 | Brzezinski | A61B 18/1206 606/40 |
| 2016/0220314 A1* | 8/2016 | Huelman | A61B 34/20 |
| 2017/0011210 A1 | 1/2017 | Cheong et al. | |
| 2017/0312043 A1 | 11/2017 | Ogawa et al. | |
| 2023/0106285 A1 | 4/2023 | Schwab | |

OTHER PUBLICATIONS

International Search Report and Written Opinion for Application No. PCT/US2017/066442, mailed on Apr. 9, 2018, 16 pages (ISRG08050/PCT).

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

FIG. 4
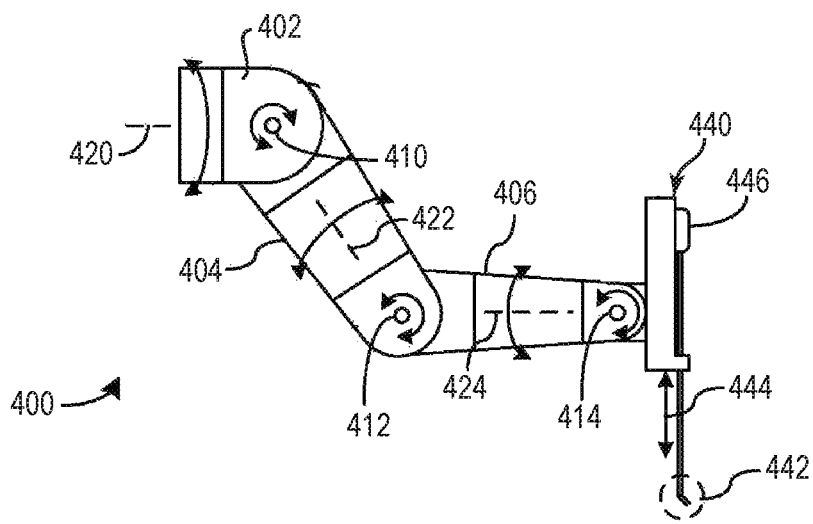
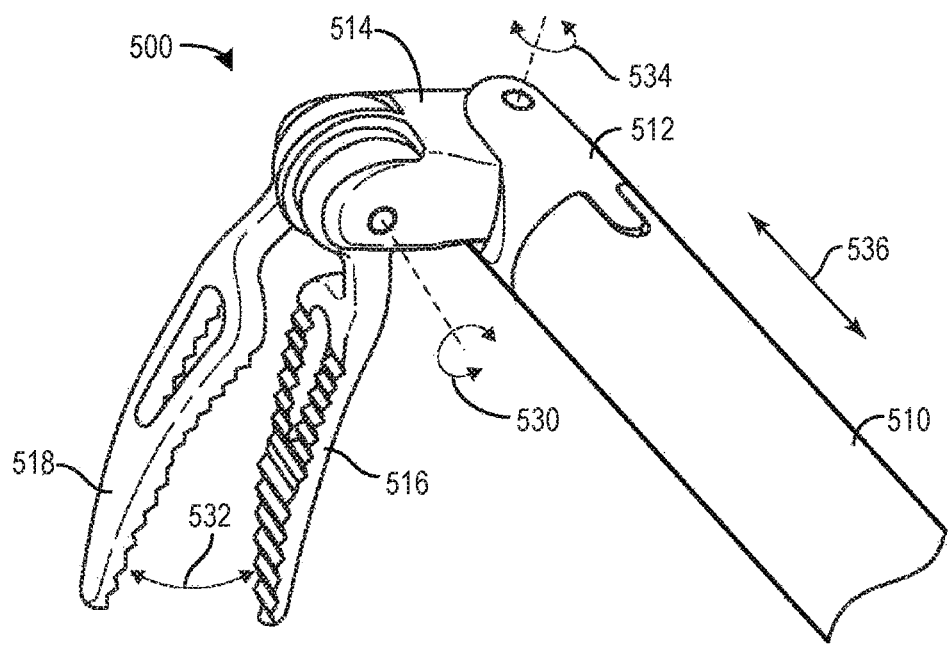
FIG. 5

DETECTION OF USER TOUCH ON CONTROLLER HANDLE

CROSS-REFERENCE TO RELATED APPLICATIONS

The present application is a continuation of U.S. patent application Ser. No. 18/073,329, filed on Dec. 1, 2022, which is a continuation of U.S. patent application Ser. No. 16/470,049, filed on Jun. 14, 2019 (now U.S. Pat. No. 11,559,364), which is a U.S. National Stage Filing under 37 U.S.C. 371 from International Patent Application No. PCT/US2017/066442, filed on Dec. 14, 2017, and published as WO 2018/112216 on Jun. 21, 2018, which claims priority to U.S. Provisional Patent Application No. 62/434,990, filed Dec. 15, 2016 and titled "Detection of User Touch on Controller Handle," all of which are hereby incorporated by reference in their entirety.

BACKGROUND

Teleoperated mechanisms allow a user to remotely control various types of mechanisms and instruments. Teleoperated surgical devices, for example, can use various types of medical instruments to perform minimally invasive surgical procedures that minimize damage to healthy tissue of patients. Control of the medical instruments at a slave device can be provided to an operator at one or more master controllers, e.g., at a remote operator terminal or station, where actuators of the slave device are controlled by the master controller to cause motion of an end effector at the slave device that interacts with the patient surgical site. In some examples, the master controller at the operator station can be physically manipulated by the operator in one or more degrees of freedom to control the end effector to be moved in coordination with the manipulation of the controller, e.g., to move in corresponding degrees of freedom at the operating site.

In some teleoperated systems, the controlled slave device is desired to be disconnected from control by the master controller during non-operation of the teleoperated system and other times or modes, e.g., when a medical procedure is not actively being performed by the system or the end effector is otherwise not desired to be controlled. For example, this disconnection can be implemented in a non-controlling mode (e.g., safe mode) that prevents unintentional control and movement of the slave device and end effector during such times. In some implementations, the non-controlling mode is a default mode of the system, and an operator is required to perform particular commands to indicate that he or she is ready to control the end effector with the master controller, e.g., to activate a controlling mode. For example, the operator may be required to perform one or more particular motions or other maneuvers with the master controllers to indicate that the master controllers are being grasped by the operator and that the operator desires the system to enter the controlling mode. However, such master controller manipulations can be time consuming and may distract the operator from the medical procedure being performed, especially if control of the end effector is interrupted multiple times during a procedure.

Some previous implementations have used techniques to detect a touch of an operator's hand on a handle to allow movements of the handle to affect movements of an end effector. For example, U.S. Pat. No. 6,587,750 to Intuitive Surgical, Inc. describes inducing a vibration on a handle and sensing a change in vibration to detect the operator's touch on the handle.

SUMMARY

Implementations of the present application relate to detection of user touch on a controller handle. In some implementations, a method includes activating a non-controlling mode of a control system. The control system includes a handle manually moveable by a user in one or more physical degrees of freedom. In the non-controlling mode, one or more actuators are controlled to cause a vibration to be provided on the handle. The method senses the vibration with one or more sensors, and determines that a difference in the vibration has occurred relative to a reference vibration using the one or more sensors, where the difference satisfies one or more predetermined thresholds. The method activates a controlling mode of the system in response to determining the difference in the vibration, and modifies the vibration on the handle in response to detecting the change in the vibration.

Various implementations and examples of the method are described. For example, in some implementations, the vibration is applied in at least one of the one or more degrees of freedom of the handle, and the sensing includes sensing the vibration in the at least one degree of freedom of the handle. In some examples, the one or more predetermined thresholds are configured to be indicative of the user touching the handle, and/or the modifying of the vibration includes removing the vibration from the handle. For example, the removing of the vibration is performed after a predetermined time period after sensing the change in vibration. In some implementations, the vibration is applied by applying a periodic control signal to the one or more actuators coupled to the handle. In some implementations, the vibration is configured to be perceived by the user while touching the handle.

Some implementations apply the vibration by applying a periodic control signal to the one or more actuators coupled to the handle, and the difference in the vibration includes a dampening of the vibration from a higher sensed amplitude to a lower sensed amplitude, where the lower sensed amplitude is below one of the predetermined thresholds. In some implementations, the difference in the vibration includes a change in a position of the handle about which the handle is vibrated in at least one of the one or more degrees of freedom, and the method further includes determining a mean position of the handle in the at least one degree of freedom, where the change in mean position of the handle satisfies one of the one or more predetermined thresholds by being greater than a mean position threshold.

In some examples, the handle is provided with one or more additional degrees of freedom by one or more additional links coupled to the handle, where the one or more additional links are provided with one or more associated sensors configured to sense motion of the one or more additional links in the one or more additional degrees of freedom. In some implementations, the additional links are decoupled from the vibration such that the vibration on the handle is not sensed by the one or more associated sensors, and motion of the additional links caused by the user does not cause motion on the handle that satisfies the one or more predetermined thresholds.

In various implementations, the modifying is a removal of the vibration from the handle, and the method further includes applying an additional vibration after the removal and comparing the additional vibration to at least one predetermined threshold, and activating the non-controlling mode of the control system based at least in part on the comparison. In some implementations, the method further includes sensing a user in physical proximity to the handle using one or more user presence sensors, where the applying of the vibration can be initiated in response to sensing the user using the one or more user presence sensors. In some examples, the method further includes changing the frequency or amplitude of the vibration in response to detecting a different operating mode of the control system.

In some implementations, activating the controlling mode includes controlling one or more actuators of a slave device to physically move at least a portion of the slave device in correspondence with physical manipulation of the handle by the user. For example, the at least one degree of freedom can include a rotational degree of freedom of the handle. In some examples, the handle includes two pincher grips, where the one or more degrees of freedom include at least one rotational degree of freedom of at least one of the two pincher grips moving in a pincher motion of the two pincher grips, and the threshold is satisfied in response to the user touching either of the two pincher grips. In some implementations, the handle is mechanically ungrounded.

In some implementations, a system includes a handle manually moveable in one or more physical degrees of freedom by a user, one or more actuators coupled to the handle and operative to output force on the handle, one or more sensors operative to sense motion of the handle, and at least one controller coupled to the one or more actuators. During a non-controlling mode of the system in which the handle is disabled from controlling motion of a device, the controller is configured to control at least one of the one or more actuators to apply a vibration to the handle, and sense a change in the vibration based on signals from the one or more sensors, where the change satisfies one or more predetermined thresholds. The controller causes activation of a controlling mode of the system in response to detecting the change in the vibration, where the controlling mode enables the handle to control motion of the device, and modifies the vibration on the handle in response to detecting the change in the vibration.

Various implementations and examples of the system are described. In some examples, the controller is further configured to sense a change in a position of the handle about which the handle is vibrated in at least one of the one or more degrees of freedom, and to determine a mean position of the handle in the at least one degree of freedom in which the handle is vibrated, where the determined change in mean position of the handle is greater than a mean position threshold. In some implementations, the controller is further configured to sense the user in physical proximity to the handle using one or more user presence sensors, where the applying of the vibration is initiated in response to sensing the user using the one or more user presence sensors. In some examples, the modification of the vibration on the handle includes controlling the at least one actuator to apply a second vibration to the handle, the second vibration having a different amplitude, a different frequency than the first vibration, and/or a combination of the different amplitude and the different frequency.

In some implementations, a method includes activating a non-controlling mode in which a handle of the master controller is manually moveable by a user in one or more physical degrees of freedom without moveably controlling a device. In the non-controlling mode, the method applies periodic forces to the handle in one or more degrees of freedom of the handle using one or more actuators in response to sensing a presence of a user relative to the master controller with one or more user presence sensors. The method senses movement of the handle caused by the periodic forces with one or more sensors configured to sense motion of the handle in the one or more degrees of freedom, and detects a change in the movement of the handle using the one or more sensors, where the change is greater than a threshold amount. In response to detecting the change in the motion of the handle, the method activates a controlling mode in which the handle is moveable by the user in the one or more degrees of freedom to moveably control the device.

BRIEF DESCRIPTION OF THE DRAWINGS

FIG. 4 is a diagrammatic illustration of an example arm assembly or portion thereof, which can be used for one or more of the arm assemblies of the manipulator slave device shown in FIG. 1, according to some implementations;

FIG. 5 is a perspective view of one example of an end effector, which can be used with one or more of the arm assemblies of the manipulator slave device shown in FIG. 1, according to some implementations;

DETAILED DESCRIPTION

Figure 1:
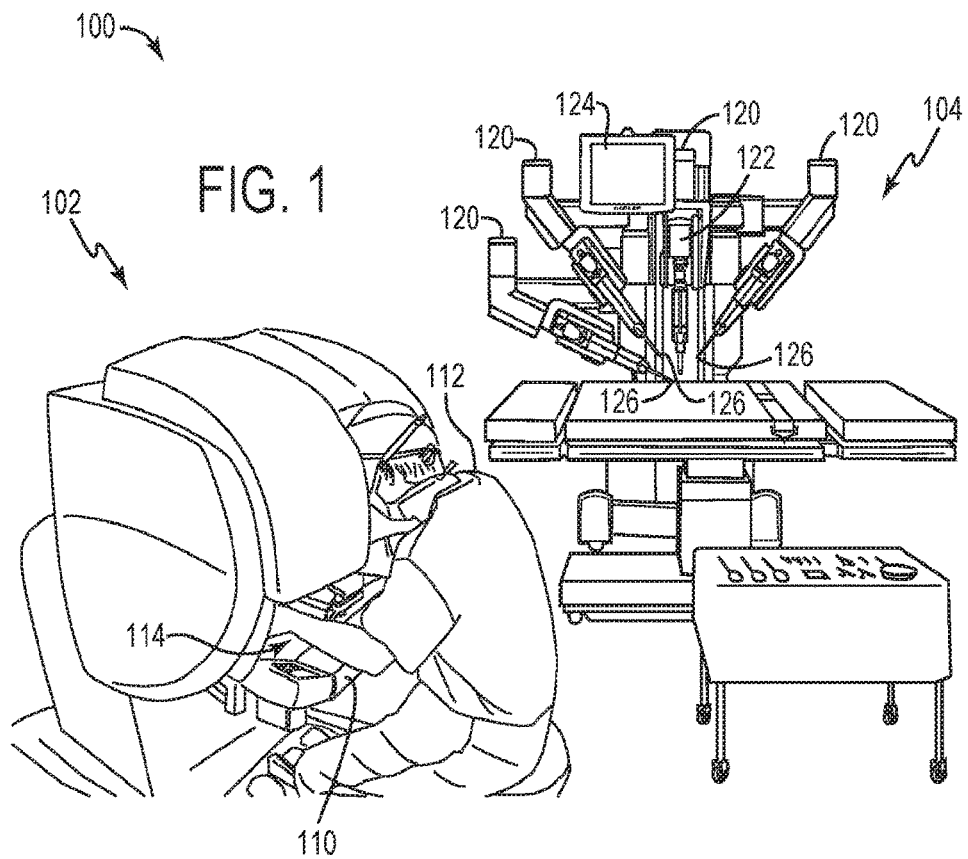
FIG. 1 is a diagrammatic illustration of an example implementation of a teleoperated surgical system which can be used with one or more features disclosed herein, according to some implementations.

One or more implementations described herein relate to detection of user touch on a controller handle. In some implementations, a control system includes a handle manually moveable by a user in one or more physical degrees of freedom. For example, the control system can be a teleoperated control system in which a master controller handle can control movement of a slave device based on the movement of the handle. A non-controlling mode of the system is activated, and a vibration is applied using one or more actuators, where the vibration is transmitted to the handle. For example, the vibration can be provided in one or more degrees of freedom of the handle. The vibration is sensed with one or more sensors, where the vibration is a reference vibration having particular characteristics if no user is touching or holding the handle. A difference or change in the vibration is detected relative to the reference vibration, e.g., when a user touches or grasps the handle. If the change in vibration satisfies a threshold, a controlling mode is activated for the control system. For example, the controlling mode allows the handle to control motion of the slave device. The vibration is removed from the handle in response to detecting the change in vibration.

Various other features are also disclosed. For example, the vibration can be removed after a predetermined time period after sensing the change in vibration. The vibration can be an initial vibration, and the system can apply an additional vibration after the removal of the initial vibration. For example, the system can determine whether the additional vibration is changed from the initial vibration that satisfied the threshold. If it is not changed by the threshold amount, then a lack of user touch may be indicated, and in some implementations the system can activate the non-controlling mode of the system. The difference or change in the vibration that indicates user touch of the handle can include a dampening of amplitude of the vibration to an amplitude below a threshold amplitude. Alternatively or additionally, the difference or change in vibration can include a change in a position of the handle in a degree of freedom in which the handle is vibrated. For example, a mean position of the handle can be determined in the degree of freedom in which the handle is vibrated, and if the change in mean position is greater than a mean position threshold, user touch of the handle is indicated.

Described features also include sensing a user in physical proximity to the handle using one or more user presence sensors. For example, a user can be sensed whether he or she is in a proper position to operate the master controller, e.g., his or her head sensed within a viewing recess of a master control workstation. The applying of the vibration to the handle is initiated in response to sensing the user using the one or more user presence sensors. In some implementations, the vibration is output at an amplitude and/or frequency so that it can be felt by the user when touching the handle. When the vibration is removed after detecting the user touch, the user is thus informed haptically that the controlling mode of the system has been activated. Some implementations can vary characteristics of the vibration while the user is touching the handle to haptically signal different modes of operation of the system or other status events to the user. Some implementations can output vibrations that are not detectable by a user touching the handle.

Features described in this disclosure allow a control system to automatically determine and provide appropriate control modes based on the sensing of user touch on a master controller. For example, a controlling mode can automatically be activated in response to a user grasping a handle of the master controller. A user thus need not manipulate a master control handle in a particular way to signal to the system that the user has grasped the handle and is ready to control a slave device or perform another function. This allows an operator to enter controlling mode more rapidly, which improves the overall workflow in the operation of the system, e.g., in a medical procedure. In addition, described features allow existing sensors and actuators to be used to detect the user's touch on the master controller handle, e.g., sensors and actuators which are already used to sense handle position and provide forces to the handle as force feedback, gravity or force compensation, etc. Therefore, no additional components and accompanying cost are required. Furthermore, user touch is sensed accurately and consistently based on sensing amplitude of a vibration as well as sensing handle position for the vibration. Furthermore, user presence can be detected with presence sensors to indicate when to apply a vibration to the handle to detect potential user touch of the master controller. One or more features disclosed herein also can determine when a user removes his or her grasp of the master controller handle, thus indicating, at least in part, to exit the controlling mode and activate a non-controlling mode.

The terms "center," "parallel," "perpendicular," "aligned," or particular measurements in degrees, Hertz, or other units as used herein need not be exact and can include typical engineering tolerances.

FIG. 1 is a diagrammatic illustration of an example teleoperated surgical system 100 which can be used with one or more features disclosed herein. Teleoperated surgical system 100 includes a master control workstation (e.g., surgeon's console) 102 and a manipulator slave device 104.

In this example, the master control workstation (e.g., surgeon's console) 102 includes a viewer 213 (shown in FIG. 2) where an image of a worksite is displayed during an operating procedure using the system 100. For example, the image can depict a surgical site during a surgical procedure. A support 110 is provided on which a user 112, e.g., an operator such as a surgeon, can rest his or her forearms while gripping two master controllers 210 and 212 (shown in FIG. 2), one in each hand. The master controllers are positioned in a workspace 114 disposed inwardly beyond the support 110. When using the workstation 102, the user 112 can sit in a chair in front of the workstation, position his or her eyes in front of the viewer and grip the master controllers, one in each hand, while resting his or her forearms on the support 110. Additional details are described below with reference to FIG. 2.

A manipulator slave device 104 is also included in the teleoperated system 100. During a surgical procedure, the slave device 104 can be positioned close to a patient (or simulated patient) for surgery, where it can remain stationary until a particular surgical procedure or stage of a procedure is completed. Manipulator slave device 104 can include one or more arm assemblies 120. In some examples, one of the arm assemblies 120 can be configured to hold an image capturing device, e.g., an endoscope 122, which can provide captured images of a portion of the surgical site. In some implementations, the captured images can be transmitted to the viewer of the workstation 102 and/or transmitted to one or more other displays, e.g., a display 124 coupled to the slave device 120. In some examples, each of the other arm assemblies 120 may include a surgical tool 126. Each surgical tool can include a surgical end effector, e.g., for treating tissue of the patient.

In this example, the arm assemblies 120 can be caused to move and articulate the surgical tools 126 in response to manipulation of the master controllers 210 and 212 at the workstation 102 by the user 112, e.g., so that the user 112 can direct surgical procedures at internal surgical sites through minimally invasive surgical apertures. For example, one or more actuators coupled to the arm assemblies 120 can output force to cause links or other portions of the arm assemblies to move in particular degrees of freedom in response to control signals received from the workstation 102. The workstation 102 can be used within a room (e.g., an operating room) with the slave device 104 or can be positioned more remotely from the slave device 102, e.g., at a different location than the slave device.

Some implementations of the teleoperated system 100 can provide different modes of operation. In some examples, in a non-controlling mode (e.g., safe mode) of the teleoperated system 100, the controlled motion of the manipulator slave device 104 is disconnected from the master controllers of the workstation 102 in disconnected configuration, such that movement and other manipulation of the master controls does not cause motion of the manipulator slave device 104. In a controlling mode of the teleoperated system (e.g., following mode), the motion of the manipulator slave device 104 is controlled by the master controls 210 and 212 of the workstation 102 such that movement and other manipulation of the master controllers causes motion of the manipulator slave device 104, e.g., during a surgical procedure. As described herein, the system can include one or more features allowing the system to determine whether a user is using master controllers and to thereby determine whether to set the system in non-controlling mode or controlling mode.

Some implementations can be or include a teleoperated medical system such as a da Vinci® Surgical System (e.g., a Model IS3000 or IS4000, marketed as the da Vinci® Si® or da Vinci® Xi® Surgical System), commercialized by Intuitive Surgical, Inc. of Sunnyvale, California. However, features disclosed herein may be implemented in various ways, including teleoperated and, if applicable, non-teleoperated (e.g., locally-controlled) implementations. Implementations on da Vinci® Surgical Systems are merely exemplary and are not to be considered as limiting the scope of the features disclosed herein. For example, different types of teleoperated systems having slave devices at worksites can make use of user detection features described herein. Other, non-teleoperated systems can also use one or more described features, e.g., various types of control devices, peripherals, etc.

In some implementations, a controlled slave manipulator device can be a virtual representation of device, e.g., presented in a graphical simulation provided by a computing device coupled to the teleoperated system 100. For example, a user can manipulate the master controls 210 and 212 of the workstation 102 to control a displayed representation of an end effector in virtual space of the simulation, similarly as if the end effector were a physical object coupled to a physical slave device.

Figure 2:
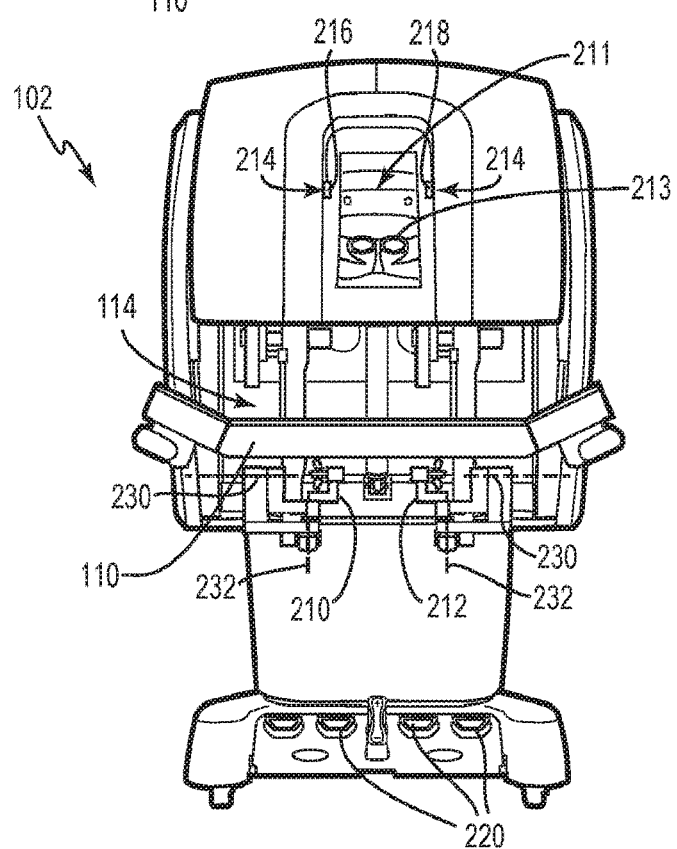
FIG. 2 is a front elevational view of an example master control workstation as shown in FIG. 1, according to some implementations.

FIG. 2 is a front elevational view of an example master control workstation 102 as described above for FIG. 1. Master control workstation 102 includes a viewer 213, where an image of a worksite can be displayed during a procedure using the teleoperated system 100. For example, images depicting a surgical site can be displayed during a surgical procedure. The viewer 213 can be positioned within a viewing recess 211 in which the user can position his or her head to view images displayed by the viewer 213. When using the workstation 102, the user 112 can sit in a chair in front of the workstation and position his or her head within the recess 211 such that his or her eyes are positioned in front of the viewer 213.

In some implementations, one or more user presence sensors 214 can be positioned at one or more locations of the master control workstation 102 to detect the presence of a user located next to or near to the workstation 102. In this example, the user presence sensors 214 can sense a presence of a user's head within the recess 211. For example, an optical sensor can be used for a presence sensor, where the optical sensor includes an emitter 216 and a detector 218. A beam of infrared or other wavelength of light is emitted from one side of the recess 211 by the emitter 216, and the beam is detected on the other side of the recess by the detector 218. If the beam is interrupted from detection by the detector, the system determines that a user's head is within the recess and that the user is in a proper position to use the master controllers of the master control workstation 102.

Additional or alternative types of presence sensors can be used in various implementations. For example, sensors can be positioned at other locations on a master controller 210 or 212 or master control workstation 102, on one or more structures within the same environment as the master control workstation 102 (e.g., operating room), or other locations.

Two master controllers 210 and 212 are provided for user manipulation. In some implementations, each master controller 210 and 212 can be configured to control motion and functions an associated arm assembly 120 of the manipulator slave device 104. For example, a master controller 210 or 212 can be moved in a plurality of degrees of freedom to move a corresponding end effector of the slave device 104 in corresponding degrees of freedom. The master controllers 210 and 212 are positioned in workspace 114 disposed inwardly beyond the support 110. For example, a user 112 can rest his or her forearms while gripping the two master controllers 210, 212, with one controller in each hand. The user also positions his or her head within the viewing recess 211 to view the viewer 213 as described above while manipulating the master controllers 210 and 212. Some examples of master controller portions are described below with reference to FIG. 3.

Some implementations of workstation 102 can include one or more foot controls 220 positioned below the master controls 210 and 212. The foot controls 220 can be depressed, slid, and/or otherwise manipulated by a user's feet to input various commands to the teleoperated system while the user is sitting at the master control workstation 102.

Figure 3:
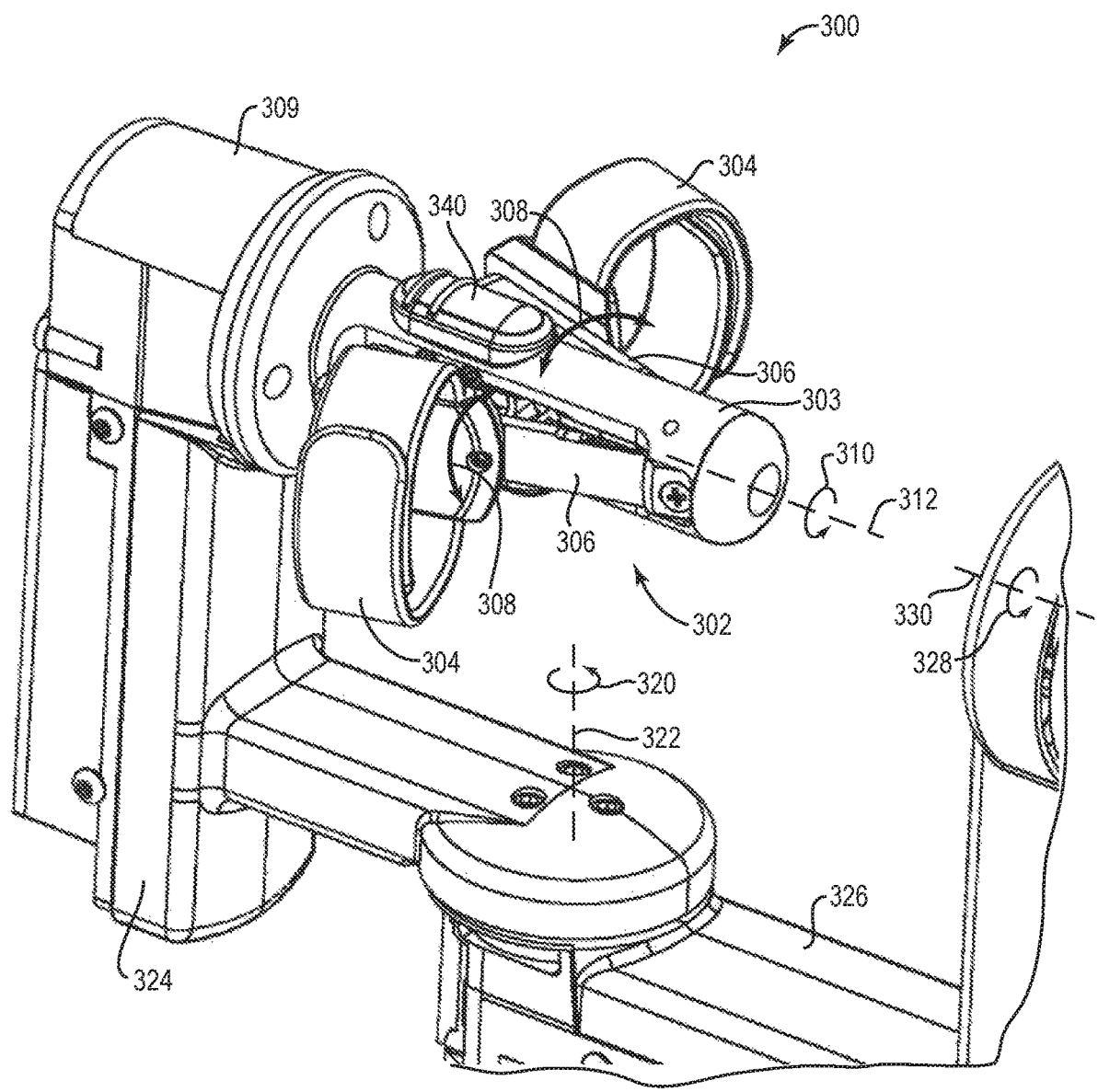
FIG. 3 is a perspective view of an example of a portion of a master controller which can be used with one or more features described herein, according to some implementations.

FIG. 3 is a perspective view of an example of a portion 300 of a master controller which can be used with one or more features described herein. In some implementations, master controller portion 300 can be used as a portion of a master controller 210 or 212 as described above with reference to FIGS. 1 and 2. In some implementations, the master controller portion 300 includes a gimbal mechanism.

Master controller portion 300 includes a handle 302 which is contacted by a user to manipulate the master controller 300. In this example, the handle 302 includes two grips that each include a finger loop 304 and grip link 306. The two grip links 306 are positioned on opposite sides of a central portion 303 of the handle 302, where the grip links 306 can be grasped, held, or otherwise contacted by a user's fingers. The two finger loops 304 are attached to grip links 306 and can be used to secure a user's fingers to the associated grip links 306. The user may also contact other portions of handle 302 while grasping the grip links 306. The grip links 306 are pivotally attached to the central portion 303 of the handle 302. Each grip link 306 and finger loop 304 can be moved in an associated degree of freedom 308 by a user, where the grip links 306 can be moved simultaneously in a pincher-type of movement (e.g., toward or away from each other). In various implementations, a single grip link 306 and finger loop 304 can be provided, or only one of the grip links 306 can be moved in the degree of freedom 308 while the other grip link 306 can be fixed with reference to the handle 302.

One or more sensors (not shown) coupled to the handle 302 can detect the positions of the grip links 306 and send signals describing the positions to one or more control circuits of the teleoperated system 100. The control circuits can provide control signals to the slave manipulator device 104. For example, the positions of the grip links 306 in degree of freedom 308 can be used to control any of various degrees of freedom of an end effector of the slave manipulator device 104, some examples of which are described below. Some implementations of the controller 300 can provide one or more passive actuators (e.g., springs) between the grip members 306 and the central portion 303 of the handle 302 to provide resistance in particular directions of the grips (e.g., movement in directions toward each other in degree of freedom 308). Some implementations can provide one or more active actuators (e.g., motors, voice coils, etc.) to output forces on the grip links 306 in the degree of freedom 308. For example, a sensor and/or actuator can be housed in central portion 303 or in housing 309 and coupled to the grip links 306 by a transmission.

The handle 302 of example master controller portion 300 can additionally be provided with a rotational degree of freedom 310 about an axis 312 extending approximately along the center of the central portion 303 of handle 302. A user can rotate the grip links 306 as a single unit around the axis 312 to provide control of, e.g., an end effector of the manipulator slave device 104 or other element of the slave device.

One or more sensors (not shown) can be coupled to the handle 302 to detect the rotation and/or position of the handle 302 in the rotational degree of freedom 310. For example, the sensor can send signals describing the position to one or more control circuits of the teleoperated system 100 which can provide control signals to the slave device 104 similarly as described above. For example, degree of freedom 310 can control a particular degree of freedom of an end effector of the slave device that is different than a slave degree of freedom controlled by degree of freedom 308 of the grip links 306.

Some implementations of the controller 300 can provide one or more actuators to output forces on the handle 302 (including grip links 306 and finger loops 304) in the rotational degree of freedom 310. For example, a sensor and/or actuator can be housed in housing 309 and coupled to the handle 302 by a shaft extending through the central portion 303 of the handle 302.

In various implementations, the handle 302 can be provided with additional degrees of freedom. For example, a rotational degree of freedom 320 about an axis 322 can be provided to the handle 302 at a rotational coupling between an elbow shaped link 324 and a link 326, where the elbow shaped link 324 is coupled to the handle 302 (e.g., at housing 309). For example, axis 322 can be similar to axis 232 shown in FIG. 2. Additional degrees of freedom can similarly be provided. For example, link 326 can be elbow-shaped and a rotational coupling can be provided between the other end of link 326 and another link (not shown). A rotational degree of freedom 328 about an axis 330 can be provided to the handle 302 at the rotational coupling. For example, axis 330 can be similar to axis 230 shown in FIG. 2. In some examples, the master controller 300 can allow movement of the handle 302 within the workspace 114 of the master control workstation 102 with a plurality of degrees of freedom, e.g., six degrees of freedom including three rotational degrees of freedom and three translational degrees of freedom. This allows the handle 302 to be moved to any position and any orientation within its range of motion. One or more additional degrees of freedom can be sensed and/or actuated similarly as described above for the degrees of freedom 308 and 310. In some implementations, each additional degree of freedom of the handle 302 can control a different slave degree of freedom of an end effector of the slave device 104.

In some implementations, handle 302 can also include one or more buttons 340, e.g., coupled to the central portion 303 or to mechanisms within central portion 303. For example, two buttons 340 can each be positioned on opposite sides of axis 312, or additional buttons can be provided. In some examples, button 340 can slide parallel to the axis 312, e.g., as directed by a user's finger, or the button can be depressed. The button 340 can be moved to various positions to provide particular command signals, e.g., to select functions, options, or modes of the control console and/or master controller (e.g., a controlling mode or non-controlling mode as described below), to command a slave device or other system in communication with the master controller, etc. Any of various types of sensors can be used to detect button manipulations, such as optical sensors, mechanical switches, magnetic sensors, etc.

One or more features described herein can be used with other types of master controllers. For example, ungrounded master controllers can be used, which are free to move in space and disconnected from ground. In some examples, one or more handles similar to handle 302 and/or grip links 306 can be coupled to a mechanism worn on a user's hand and which is ungrounded, allowing the user to move grips freely in space. In some examples, the positions of the grips can be sensed by a mechanism coupling the grips together and constraining their motion relative to each other. Some implementations can use glove structures worn by a user's hand. Furthermore, some implementations can use sensors coupled to other structures to sense the grips within space, e.g., using video cameras or other sensors that can detect motion in 3D space. Some examples of ungrounded master controllers are described in U.S. Pat. Nos. 8,543,240 and 8,521,331, both incorporated herein by reference. The detection of user touch described herein can be used with ungrounded master controllers. For example, vibration can be applied to a handle (e.g., grip) by one or more actuators coupled to the handle, and this vibration can be sensed similarly as described herein to determine if the handle is contacted or grasped by the user.

FIG. 4 shows an example arm assembly 400 or portion thereof, which can be used for one or more of the arm assemblies 120 of the manipulator slave device 104 shown in FIG. 1. Arm assembly 400 can include multiple links 402, 404, and 406 rotatably coupled to each other. For example, link member 402 can be coupled to a grounded structure, link member 404 can be rotatably coupled to link member 402, and link member 406 can be rotatably coupled to link member 404. Each link member can be coupled to the other link member(s) at axes sensed and driven by sensors and actuators, allowing portions of arm assembly 400 to be actuated and sensed about rotational axes 410, 412, and 414. Some implementations can provide additional actuated and/or sensed motion of the arm assembly, e.g., about axes extending lengthwise through the links 402, 404, and 406, thus allowing rotation about axes 420, 422, and 424. One example of a surgical manipulator arm is a da Vinci® surgical system instrument manipulator arm available from Intuitive Surgical, Inc. of Sunnyvale, Calif.

An end effector mechanism 440 can be coupled to the end of link member 406 and provides an end effector 442 at its distal end. The end effector 442 is provided the degrees of freedom provided by the rotation of the link members 402, 404, and 406 as described above. End effector mechanism 440 additionally can provide linear motion to the end effector 442 along a linear axis 444. Furthermore, end effector mechanism 440 can provide rotational and other degrees of freedom to the end effector 442 as described below with reference to FIG. 5. In some examples, actuators and sensors included in a mechanism 446 of the end effector mechanism can provide such degrees of freedom to the end effector 442.

In some implementations, components in the arm assembly 400 can function as force transmission mechanisms to receive teleoperated servo actuation forces and redirect the received forces to operate components of the end effector 442. In some examples, end effector 442 receives multiple separate actuation inputs from the end effector mechanism 440 and/or other arm assembly components, e.g., where the number of actuation inputs depend on the number of instrument features to be controlled. In other examples, the end effector 442 can include one or more motors or other actuators that operate associated instrument features. Some implementations can control end effector features such as the pitch, yaw, and/or roll of the end effector 442, the output of material transported through a connecting tube and out of end effector 442 (e.g., liquid or other fluids), suction forces provided by end effector 442, and/or any of a multiple of other end effector functions (e.g., opening jaws of a grasper, moving a blade, etc.).

FIG. 5 is a perspective view of one example of an end effector 500. For example, end effector 500 can be used as end effector 442 of the arm assembly 400 as referenced above with respect to FIG. 4. End effector 500 is an example surgical instrument that can operate as forceps in a surgical procedure to grasp tissue, objects, etc. Other types of surgical instruments and end effectors can be used in other implementations as described elsewhere herein.

End effector 500 can be provided at a distal end of a main tube 510 which can be coupled to another portion of the end effector mechanism 440 shown in FIG. 4, for example. A proximal clevis 512 is coupled to the distal end of main tube 510, and a distal clevis 514 is rotatably coupled to the proximal clevis 512. The forceps end effector 500 includes jaws 516 and 518 that are rotatably coupled to the distal clevis 514.

The jaws 516 and 518 are provided with several physical degrees of freedom that can be manipulated by the master controllers 210 and 212 of the master control workstation 102 (shown in FIGS. 1 and 2). For example, the jaws 516 and 518 can be rotated about axis 530 of the link between the jaws and the distal clevis 514, e.g., to open and close the jaws with respect to each other as shown by arrow 532, and/or to rotate the jaws in conjunction to a different rotational position. In addition, the jaws 516 and 518 can be rotated about axis 534 of the link between distal clevis 514 and proximal clevis 516, e.g., to rotate the jaws in space. In addition, the jaws 516 and 518 can be translated along linear axis 536, which in some implementations can correspond to the linear axis 444 shown in FIG. 4.

In some implementations, one or more of the degrees of freedom of the end effector 500 can be controlled using tendons, e.g., cables (not shown), that are mechanically coupled to one or more of the elements 514, 516, and 518 and extend through tube 510 to a transmission or other mechanism. For example, the tendons can be coupled to pulleys and/or other transmission elements driven by actuators and sensed by sensors provided in mechanism 446 coupled to arm assembly 400 as shown in FIG. 4.

In some examples, the end effector 500 can be inserted through a patient's body wall to reach a surgical site. In some implementations, main tube 510 may include a cavity that can provide material transfer along the tube. For example, material may be transferred between a distal end and a proximal end of tube 510, or points near the proximal end and near the distal end of tube 510. For example, main tube 510 (or other tube) can couple a surgical irrigation fluid (liquid or gas) source (not shown) to the end effector 500 so that irrigation fluid can be routed from a source through the main tube to exit via end effector 500. Similarly, main tube 510 can couple a surgical suction source (not shown) to end effector 500 so that material from a surgical site can be drawn into end effector 500 and through tube 510 to the source. Other types of connection features can be provided in other implementations.

Other types of arm assemblies and end effector mechanisms can be used in other implementations. For example, end effector mechanisms can include flexible elements, articulated "snake" arms, steerable guide tubes, catheters, scalpel or cutting blade, electro-surgical elements (e.g., monopolar or bipolar electrical instruments), harmonic cutter, scissors, forceps, retractors, dilators, clamps, cauterizing tools, needles, needle drivers, staplers, drills, probes, scopes, light sources, guides, measurement devices, vessel sealers, laparoscopic tools, or other tip, mechanism or device.

Figure 6:
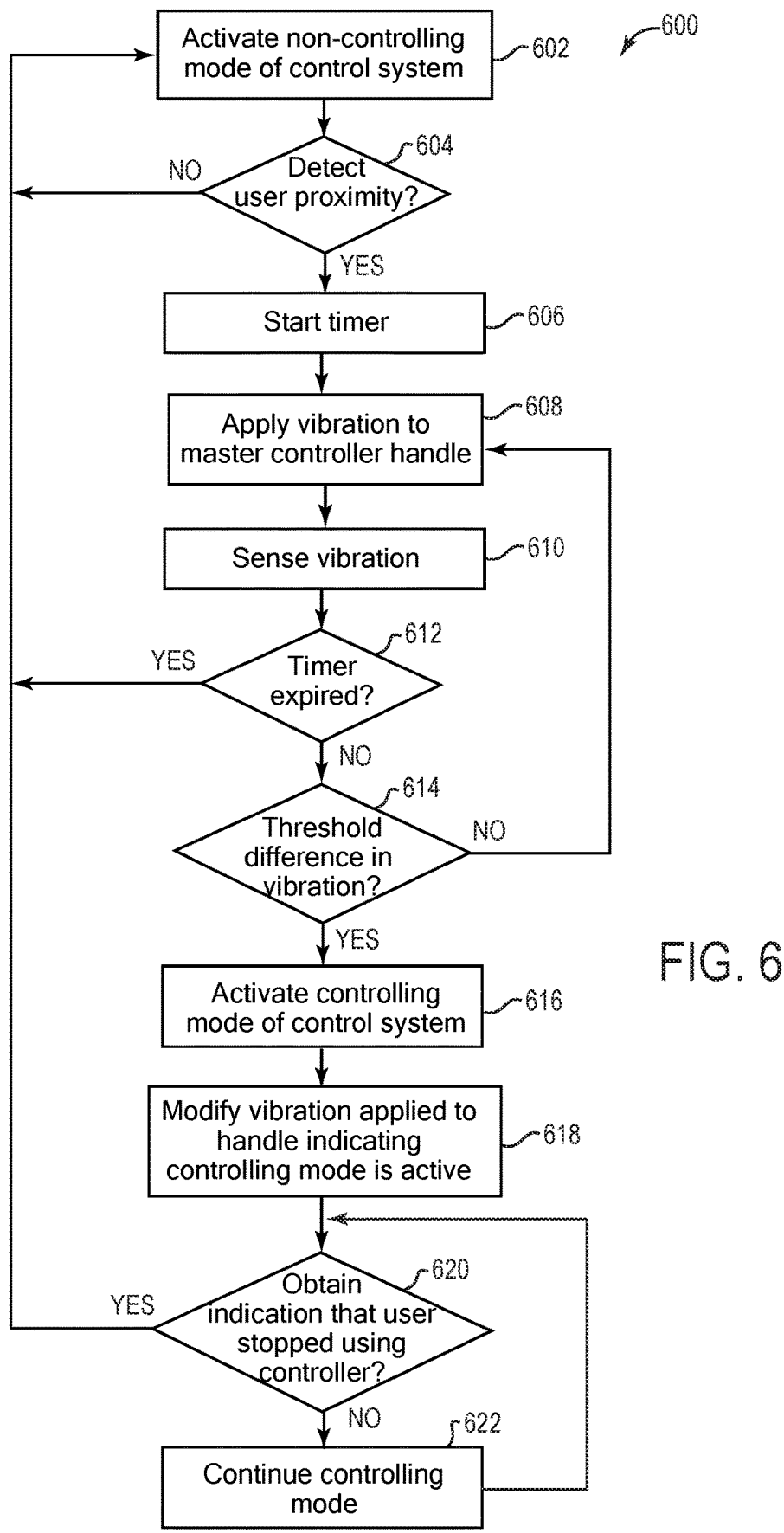
FIG. 6 is a flow diagram illustrating an example method to detect user touch on a master controller, according to some implementations.

FIG. 6 is a flow diagram illustrating an example method 600 to detect user touch on a master controller. Method 600 can, for example, be performed by a controller circuit component of the master control workstation 102. In some examples, the controller can be one or more processors, e.g., microprocessors or other controllers, some examples of which are described below with reference to FIG. 9. A single master controller is referred to in method 600 for explanatory purposes. The master controller can be, for example, a master controller portion 300 of master controller 210 or 212, or another master controller as described herein. Multiple master controllers can be similarly processed as described in method 600, e.g., both master controllers 210 and 212 of FIG. 2.

In block 602, a non-controlling mode of the control system (e.g., teleoperated system 100) is activated. The non-controlling mode can also be considered a "safe mode" in which the master controller is not enabled to provide control signals to a controlled device such as slave device 104, even if the master controllers are manipulated by the user. Thus, for example, the controlled device is disconnected from the master controller for non-controlling mode, e.g., the device is not being controlled by the master controller. For example, the master controllers 210 and 212 can be manipulated by a user in non-controlling mode but will not cause any controlled motion of the elements of the manipulator slave device 104.

In block 604, it is checked whether user presence is detected in proximity to the master controller, e.g., master controller 210 and/or 212. For example, such proximity can indicate that a user may be ready to start using the master controller to control the slave device. In some implementations, sensors can detect a presence of a user. For example, the presence sensor 214 described above with reference to FIG. 2 can sense the presence of a user's head in a viewing recess 211 of master control workstation 102, indicating potential use of the master controllers 210 and 212 by the user. In some implementations, other sensors can be used to sense user presence as described above.

If a user has not been detected, then the method can return to block 602 to continue the non-controlling mode of the master controller. If a user has been detected, then the method continues to block 606, in which a timer is started. In some implementations, the timer can be used to provide a time limit for a time period in which the control system is receptive to detecting a user's touch on a master controller handle and activating controlling mode. For example, the timer of block 606 can be started after user proximity is detected in block 604. Some implementations can start a timer based on other or additional conditions, or at other stages of the method 600.

In block 608, vibration is caused to be applied to the handle of the master controller. For example, the vibration can include periodic forces causing an oscillation in the handle. In other implementations, other types of periodic forces can be applied. In some implementations, the method controls one or more actuators to provide the vibration in one or more degrees of freedom of the handle of the master controller. These actuated degrees of freedom can receive forces from active actuators (e.g., motors, voice coils, etc.) as controlled by signals from control electronics. The vibration of block 608 can be output using one or more existing actuators that provide forces to the handle for other purposes in normal operation, e.g., to provide force feedback to the user, to counter other forces, etc. In the master controller example of FIG. 3, the vibration can be applied in one or more degrees of freedom of the handle. In one example, the vibration can be applied as an oscillating force in the rotational degree of freedom 310 by the actuator outputting forces in that degree of freedom. In another example, the vibration can be applied as an oscillating force in the pinching degree of freedom 308 of the grip links 306 by an actuator outputting forces in that degree of freedom. Some implementations can output forces in both degrees of freedom 308 and 310, and/or in other degrees of freedom of the handle 302.

In some implementations, the vibration of block 608 can be output on the handle of the master controller directly and not in a degree of freedom of movement of the handle. For example, an actuator dedicated to providing the vibration can be coupled to a housing of the handle and controlled to oscillate (e.g., vibrate, linearly oscillate a weight, rotate a weight, etc.) to provide a vibration through the housing of the actuator and through any intermediary structures or elements, to the handle. Other actuators and mechanisms can also be used to provide vibration to the handle.

In some implementations, the vibration resulting on the master controller handle can be a sufficiently high frequency and/or low enough amplitude so as to not be perceived by a user holding, grasping, or otherwise touching the handle. For example, the vibration on the handle, which is changed by the user touching the handle (as described below), is not felt by the user. In other implementations, the vibration on the handle can be perceived by a user touching the handle. In some examples, a vibration of about 100 Hz can be output on the handle and perceived by the user. In another example, a vibration in a range of about 50-200 Hz can be output on the handle and perceived by the user. For example, the perceived vibration, or a particular amplitude and/or frequency of the perceived vibration, can indicate to the user that a particular mode of operation of the master controller is present, e.g., non-controlling mode.

In block 610, the applied vibration is sensed. For example, in implementations in which the vibration is applied in one or more degrees of freedom of the handle of the master controller, the vibration can be sensed using one or more sensors that sense motion in those degrees of freedom. Sensors that normally can be used to detect the position of the handle, can also be used to sense the vibration which causes oscillating motion of the handle in the sensed degree(s) of freedom. For example, one sensor can be used to sense the vibration in one degree of freedom. In other examples, multiple sensors can sense the vibration in multiple degrees of freedom of the handle, e.g., for redundancy and greater accuracy of sensing.

In other implementations, the vibration can be sensed using one or more sensors that do not sense motion of the handle in particular degrees of freedom. For example, a motion sensor such as a gyroscope or accelerometer can be coupled to a housing of the handle or master controller and can be used to sense vibration. Other types of sensors can also be used to sense the vibration, including optical sensors, piezo elements, etc.

Some implementations can process raw sensor signals to provide the signals in a particular amplitude range for further processing. For example, an initial part of a sensed waveform can be removed, a DC component of the signal can be removed, 0-values can be added before the signal, etc. In some implementations, the sensing of the vibration can be insensitive to motion of other components of the master controller. For example, linkages 324, 326, and other linkages of a master controller 210 and 212 that are further from a handle 302 can be moved in their axes of motion, and such movement is not sensed as vibration, nor affects the vibration, for the method 600.

If the user is not touching the handle of the master controller, the vibration sensed in block 610 can have particular characteristics, e.g., amplitude and frequency, that is in a known, expected range for the master controller handle when the handle is not being touched by a user. This known vibration waveform can be referred to as a "reference vibration" for the untouched state of the handle. This vibration is the result of the actuators used, the mechanical structure and assembly of the handle and elements coupled to the handle, and other factors, without a user touching the handle. In some implementations, known characteristics of the reference vibration can be stored in storage of the system and the stored characteristics can be used to determine thresholds and to compare with currently sensed vibration on the handle. In some implementations, the reference vibration is determined as measured by the sensors and updated each time the system is initialized or enters particular states or modes when it can be assumed that no user is touching the handle. For example, the reference vibration can be determined each time method 600 is initiated, and updated periodically when it can be assumed that no user is touching the handle.

If the user is touching the handle, the vibration sensed in block 610 will likely have different characteristics than the reference vibration. In some cases, a vibration initially sensed in method 600 is approximately the same as the reference vibration (and/or can be used as the reference vibration), before the user has touched the handle. The vibration resulting from the user touching the handle is detected as a change or difference from the reference vibration, as described below.

In block 612, it is checked whether the timer started in block 606 has expired (for some implementations including a timer). In some examples, a timer can have a time period T, e.g., in a range 5 to 10 seconds, and this time period is checked if it has elapsed. If the time period has expired, then the method returns to block 602 to activate non-controlling system and to determine if user proximity is detected. This option indicates that no user touch has been sensed within the time period T and so the method returns to block 602 to check if the user is still in proximity.

If the time period has not expired in block 612, then in block 614 it is checked whether there has been a threshold difference (e.g., change) in the vibration, as sensed by one or more sensors. For example, the threshold difference can be indicated by checking whether the currently-sensed vibration has changed in one or more characteristics relative to the reference vibration and now satisfies one or more thresholds with that change. For example, the change can be a change of a threshold amount or a change to a particular threshold value. Such a threshold difference can be considered an indication that a user is touching the handle of the master controller. For example, the amplitude of the vibration can be checked whether it has changed by a threshold amount relative to the reference vibration sensed with no user touch on the handle. In some implementations, the mean position of the handle can be checked to determine whether it has changed by a threshold amount. Some implementations can check both amplitude and mean position thresholds. Some examples of such detection are described below with reference to FIGS. 7A-7B and 8.

If no such threshold difference in the vibration has been detected, then the method returns to block 608 to continue to apply the vibration to the master controller handle. If a threshold change in the vibration has been detected, then the method continues to block 616, in which the controlling mode of the control system is activated. As described above, controlling mode allows the manipulations of the master controller to control a controlled device. For example, in a teleoperated system, the manipulations of the master controller can control corresponding motions, physical properties (heat, electricity, etc.), and/or other functions of a slave manipulator device in controlling mode, such as moving an end effector in space, opening jaws of the end effector, outputting heat or other energy from the end effector, etc.

In some implementations, the controlling mode is activated in block 616 after a predetermined amount of time has passed after detecting the threshold difference in the vibration. The amount of time can be used to more accurately determine that a true threshold change in vibration has been detected rather than a spurious signal or other effect. In addition, in some implementations, the amount of time can be used to allow the user to feel the vibration of the non-controlling mode before the vibration is removed or otherwise modified in controlling mode as an indicator of change of modes to the user (as described below). In some examples, the amount of time can be one the order of about a second, or less time if the user is not to be informed of the change in operating mode via the vibration.

In block 618, the vibration applied to the handle can be modified to indicate that the master controller has activated controlling mode, e.g., controlling mode is active. In some examples, the modification includes removing the vibration from the handle. In some implementations, this removal can indicate to the user that controlling mode is active and that the master controller now controls a device, e.g., the slave manipulator device 104. In some implementations, the modification can include a change in amplitude, frequency, and/or other characteristic(s) to indicate to the user the change to the controlling mode. In some implementations, the vibration can be changed in one or more characteristics and then removed from the handle. For example, this can be used to indicate the change to controlling mode to the user. In some examples, the vibration can be changed in one or more characteristics for a particular amount of time and then removed from the handle. For example, the previous vibration can be changed to a number of high amplitude pulses or clicks output at a lower frequency than the previous vibration, or the number of pulses or clicks can be superimposed on the previous vibration.

In block 620, it is checked whether an indication has been obtained that indicates that the user has stopped operating the master controller to control a device, e.g., a slave manipulator device 104. The indication can be implemented in different ways in various implementations. In some examples, the user can stop operating the master controller by releasing his or her touch or grip on the handle of the master controller.

The user's release of touch or grip on the handle can be detected in any of various ways. For example, in some implementations the method continues to apply a vibration to the handle during controlling mode, and a change in the amplitude, frequency, mean position, and/or other characteristic of the vibration can be checked similarly as described above. In some examples, if one or more characteristics (e.g., an amplitude) of the continuing vibration is changed (e.g., increased) sufficient to satisfy one or more thresholds (e.g., changed by a threshold amount or is changed to a particular threshold value), then this can be considered an indication that the user is no longer touching the handle or is touching the handle less strongly. This change in user touch causes the vibration to change, and the user is considered to have stopped operating the master controller. For example, the one or more thresholds can be the same as used in the detection of user touch as described above, e.g., with the use of a reference vibration known to indicate a user is not touching the handle.

In some implementations, the method modified the vibration in block 618 when activating controlling mode, e.g., removed the vibration. In some of these implementations, the method can repeatedly (e.g., periodically) apply an additional or "status" vibration to the handle after the modification while controlling mode is active to check the status of the user's touch on the handle. For example, the status vibration can be the same vibration applied in block 608, or can be a vibration having one or more characteristics different than the vibration of block 608. In some implementations, the status vibration can be output with a small amplitude and/or other characteristics so as to be imperceptible (or greatly reduced in perception) by the user (if the user is still touching the handle). In other implementations, the status vibration can be made perceptible by the user. In some implementations, the status vibration can be applied for a particular duration. For example, the duration can be short (e.g., less than one second) such that a larger-amplitude or lower frequency vibration is mostly imperceptible by the user if the user is touching the handle.

In various implementations, the method can compare the status vibration to at least one predetermined threshold. In some examples, the method can check whether the status vibration is different or changed in one or more characteristics by one or more threshold amounts as compared to a vibration when the user was touching the handle. Alternatively or additionally, the method can check whether the status vibration is the same as or within a threshold similarity to a reference vibration that is known to indicate that there is no user touch on the handle. For example, some implementations can check whether the status vibration satisfies one or more of the thresholds(s) used in block 614, and if it does not satisfy those threshold(s), it can be considered an indication that the user is not touching the handle. In some implementations, based on the comparison of the additional vibration to the at least one predetermined threshold, e.g., if one or more of these conditions are found, the method can consider the user to no longer be operating the master controller.

In some implementations, the checking of the status vibration described above can be used as a secondary or redundant check as to whether the user is still touching or operating the handle of the master controller. For example, one or more other sensors of the system can be used to detect whether the user is still touching the handle, and the status vibration can be checked to provide a confirmation of such detection.

If no indication is obtained to indicate that the user has stopped operating the master controller, then the method continues to block 622 to continue providing the controlling mode of the control system (and any controlling mode vibration on the handle, if applicable), and the method returns to block 620 to continue checking for an indication that the user has stopped operating the controller. If in block 620 an indication is obtained to indicate that the user has stopped operating the controller, then the method returns to block 602 to activate the non-controlling mode of the system. For example, the control of the slave manipulator device 104 is disconnected from the master controller based on the indication that the user is no longer operating the master controller. At block 602 and following blocks, the method can check for a user operating the master controller as described above.

Some implementations can indicate to the user via the vibration and/or other forces output on the handle of the master controller that the control system has activated a different mode of operation, e.g., indicate a change in the operating mode. Some implementations can indicate a different mode of operation by continuously providing a particular vibration during the mode. Modes of operation can include the controlling mode and non-controlling mode described herein. For example, a particular amplitude and/or frequency of a vibration perceived by the user can indicate to the user that a particular mode of operation of the master controller is active. A different amplitude and/or frequency of vibration can indicate a different mode of operation is active. In some implementations, additional modes of operation can be provided for a teleoperated system or other control system, and these modes can be indicated by different vibration characteristics. For example, a particular mode can provide control of a camera of the slave device 104 to the master controller instead of control of an end effector, or provide control over other slave device functions.

In some implementations, the handle vibration described herein can be decoupled from sensing of additional links coupled to the handle, and/or the sensing of the handle vibration as described herein can be decoupled from sensing movement of the additional links. For example, the handle of the master controller can be provided with one or more additional degrees of freedom by one or more additional links coupled to the handle, e.g., additional degrees of freedom 320 and 330 in the example of FIG. 3. The additional degrees of freedom can be provided with one or more associated sensors configured to sense motion of the one or more additional links in the one or more additional degrees of freedom. The vibration and/or the additional links can be configured such that the additional sensors do not sense the vibration output on the handle for sending user touch as described herein. In addition, the vibration on the handle can be provided with a maximum amplitude that is only sensed in the degree(s) of freedom used to detect user touch and does not cause the additional sensors to sense the handle movement caused by the vibration. Furthermore, the system can be configured such that touch and movement of the additional links by the user, e.g., to move the handle in one or more degrees of freedom, or accidental touch or movement of the additional links, does not satisfy the thresholds used for the sensing of the vibration and thus does not trigger the sensing of user touch. In some examples, an orthogonal layout of successive rotational axes, e.g., axes 312, 322, and 330, can provide such decoupling. In other implementations, a material (e.g., a softer material such as rubber or foam) can be provided within an interior or other area of one or more additional links, e.g., to absorb the vibration and reduce the effects of the vibration on the sensing of the additional links and/or reduce the effects of movement of the additional links on sensing the vibration.

The blocks described in the methods disclosed herein can be performed in a different order than shown and/or simultaneously (partially or completely) with other blocks, where appropriate. Some blocks can be performed for one portion of data and later performed again, e.g., for another portion of data. Not all of the described blocks need be performed in various implementations. In some implementations, blocks can be performed multiple times, in a different order, and/or at different times in the methods. For example, block 604 can be performed at approximately the same time as blocks 606-610, such that the controlling mode is activated in block 612 if both blocks 604 and 610 have positive results.

Figure 7A:
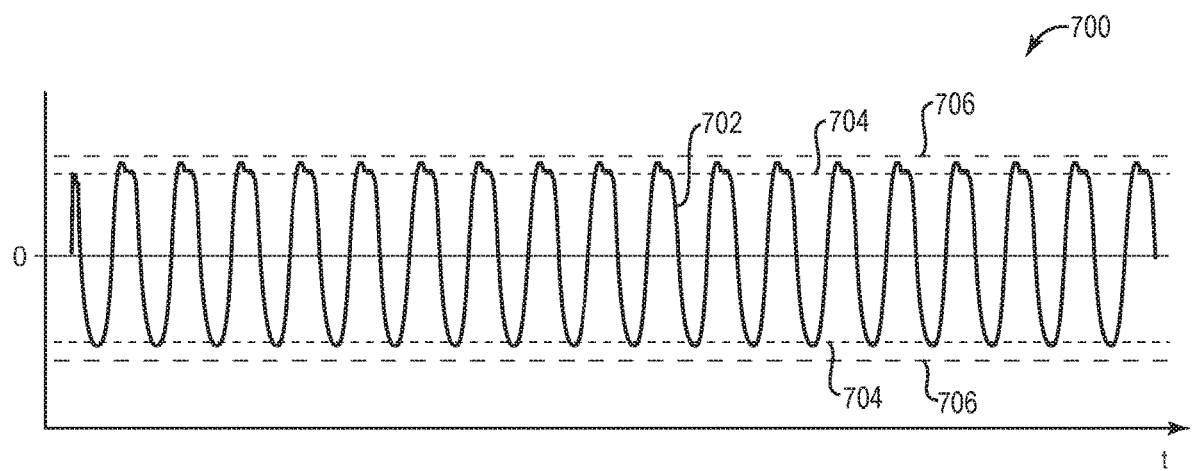
FIG. 7A shows a graph of an example vibration waveform sensed on a handle of a master controller while the user is not touching the handle, according to some implementations.
Figure 7B:
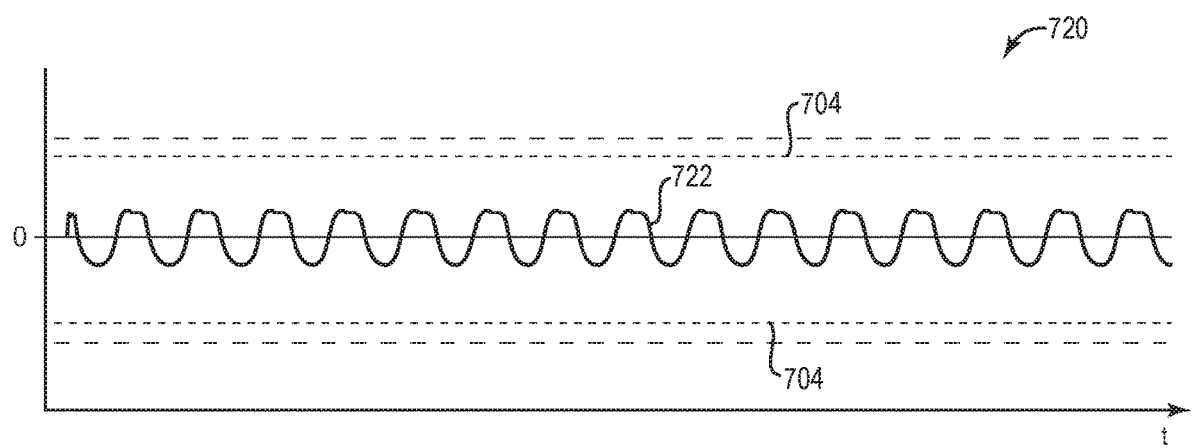
FIG. 7B shows a graph of an example waveform sensed on a handle of a master controller while the user is touching the handle, according to some implementations.

FIGS. 7A-7B are diagrammatic illustrations of graphs of example vibration waveforms that can be used to detect a user's touch on a handle of a master controller as described with reference to FIG. 6.

FIG. 7A shows a graph 700 of an example of a reference waveform 702 sensed over time in a degree of freedom of the handle while the user is not touching the handle. For example, in the example master controller 300 of FIG. 3, the reference waveform 700 can be sensed in the rotary degree of freedom 310 by sensors of the master controller. The vibration can be induced in the degree of freedom 310 by an actuator provided in that degree of freedom.

In this example, waveform 702 is sinusoidal. Other periodic waveforms can also be used. In some implementations, as described above, the vibration can be of a high enough frequency and/or low enough amplitude so as to not be felt (or to be reduced in feel) by a user touching the handle. For example, in some implementations, vibration having a frequency above about 1 kHz can be provided on the handle to reduce or eliminate user perception of the vibration; other frequencies can alternatively be used. The forces required and the control frequency of the signal used to provide this resulting vibration frequency can vary depending on the physical structure(s) to which the handle is coupled, the actuators used, etc.

Graph 700 also indicates two sets of thresholds. A lower threshold 704 is provided at positive and negative amplitudes. If the amplitude of the waveform falls below a lower threshold 704, then a detection is triggered, e.g., a user is considered to be touching and using the master controller. A higher threshold 706 can also be provided at positive and negative amplitudes. If the amplitude of the waveform falls above a higher threshold 706, then a detection is also triggered, e.g., a user is considered to be touching and using the master controller. The higher threshold 706 can be used to detect an occurrence where a user may be amplifying a signal by moving the handle, e.g., by causing motion that reinforces the vibration motion. The thresholds 704 and 706 can be tuned in various implementations to allow a particular amount or weight of user touch to trigger a detection.

In one example using a master controller similar to master controller 300, a sinusoid can be used for waveform 702 having an amplitude of 0.35 degrees in the rotary degree of freedom 310, and a frequency of 5 Hz.

FIG. 7B shows a graph 720 of an example of a waveform 722 sensed over time in a degree of freedom of the handle of a master controller after a user has touched or grasped the handle. The amplitude of the waveform 722 has dampened or reduced compared to the waveform 702 of FIG. 7A, due to the user's contact that restricts the motion of the handle caused by the vibration. In this example, the waveform 722 has been changed to have an amplitude less than the threshold 704, and so a detection is triggered, e.g., a user is considered to be touching and using the master controller. If the user removes his or her touch or grasp, a waveform approximately similar to reference waveform 702 of FIG. 7A typically returns to the handle.

Figure 8:
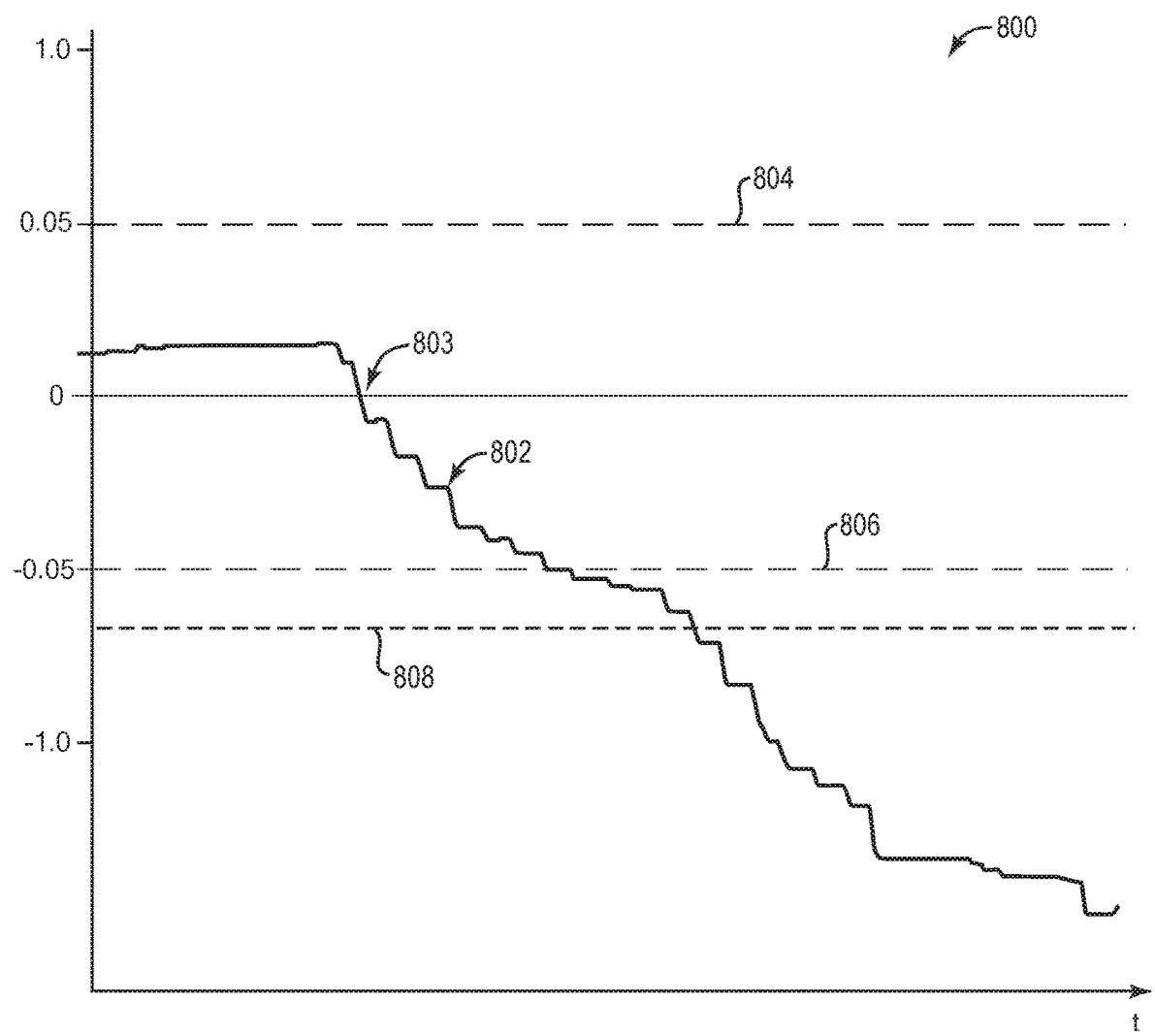
FIG. 8 shows a graph of an example waveform that can be used to detect a user's touch on a handle of a master controller based on mean position, according to some implementations.

FIG. 8 is a diagrammatic illustration of a graph 800 of an example waveform 802 that can be used to detect a user's touch on a handle of a master controller based on mean position. In this example, the position around which the handle is vibrating is sensed over time, e.g., a change in position of the vibration's center of oscillation. For example, in the example master controller 300 of FIG. 3, the rotational position of the handle in the rotational degree of freedom 310 can be sensed. In the example of graph 800, the vertical axis can be radians in the rotational degree of freedom. In another example, the position of a grip link 306 within the degree of freedom 308 can be sensed (or both grip links 306 can be sensed).

Mean thresholds 804 and 806 can be used to detect a trigger, e.g., an indication that a user is touching the handle of the master controller. A mean threshold is designated at a particular distance or angle (e.g., based on whether the degree of freedom sensed is linear or rotational, respectively) from a reference position. If a mean position of the handle satisfies the threshold, e.g., the mean position shows movement of the handle more than the threshold amount, then this can be considered a detection of a user's touch on the handle. The mean position of the handle can be the arithmetic mean of a number of sampled positions of the handle, e.g., sampled in a particular time period. In some implementations, the mean position can be based on the number of sampled positions sensed from the beginning of an ongoing time period of operation. Some implementations can determine the mean position as a rolling average position, e.g., in which a particular amount or subset of the last sampled positions are used to determine the mean position.

Waveform 802 initially shows the position of the handle a short rotational position away from a reference position 0 in a positive direction. At a point 803, the position of the handle moves to a negative position on the other side of the reference position, and the handle then continues to drift in the negative direction further from the reference position.

The mean position 808 of the handle is determined based on a recorded number or range of position samples, e.g., over a particular period of time, such as approximately the period of time shown in graph 800. In this example, the mean position 808 falls beyond the mean threshold 806 and thus satisfies the threshold. This amount of change in position is considered to indicate that a user is touching the handle.

In some implementations, the detection of the mean position can be used in conjunction with the detection of vibration amplitude as described above with reference to FIG. 6. For example, both the amplitude and the mean position of the vibration can be required to have changed by their respective threshold amounts to consider the handle to be touched by a user. This may provide a more accurate detection in some implementations, in comparison to using only amplitude or mean position. In some implementations, either the vibration or the mean position change in the threshold amount can be considered a detection of the user's touch on the handle.

In some implementations, after a user touch has been detected on the handle (e.g., during controlling mode), the mean position of the handle of the master controller can continue to be determined based on new position data describing the handle position. For example, a number of positions sampled in a particular time duration can be periodically used to determine a mean position of the handle and that mean position can be compared to the mean thresholds. If the mean position of the handle is at a position between the mean thresholds 804 and 806, then the handle can be considered to be untouched by the user, in some implementations.

Figure 9:
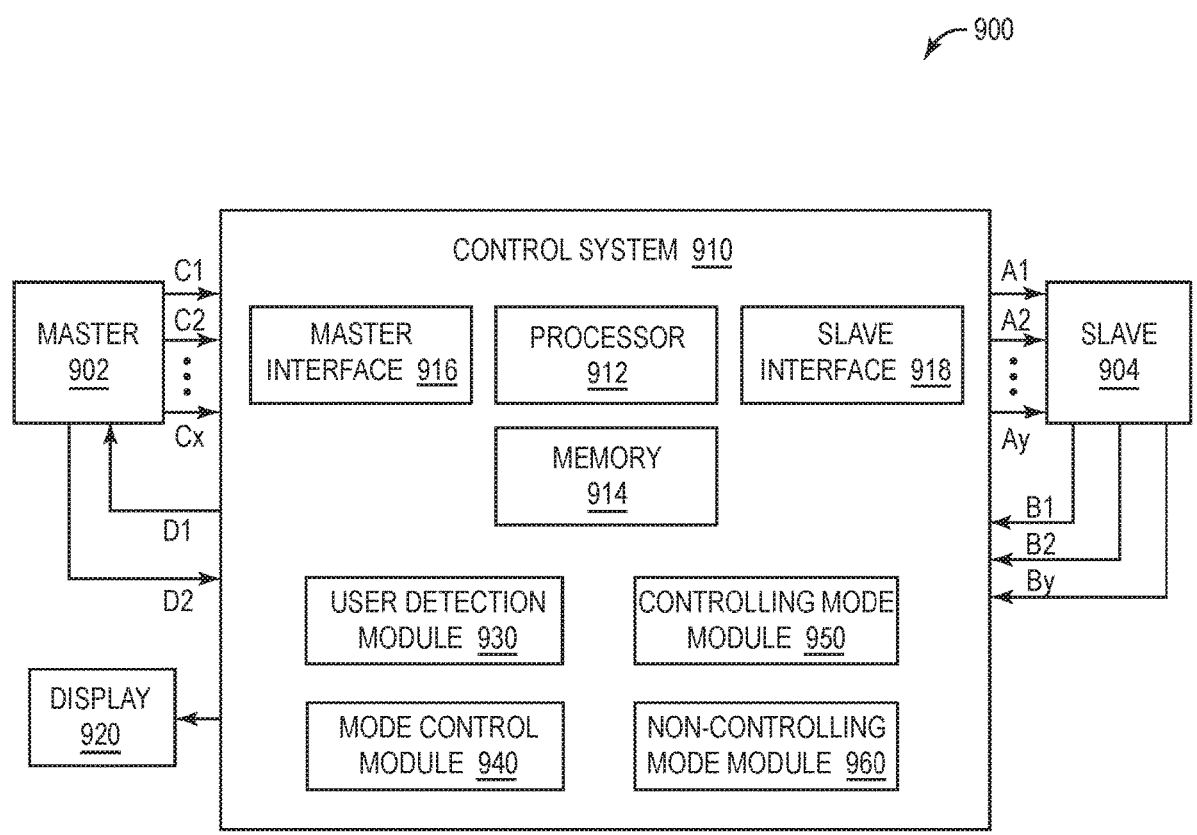
FIG. 9 is a block diagram of an example master-slave system which can be used for one or more implementations described herein.

FIG. 9 is a block diagram of an example master-slave system 900 which can be used with one or more features described herein. System 900 includes a master device 902 that a user may manipulate in order to control a slave device 904. In some implementations, master device 902 can be, or can be included in, master control workstation 102 of FIG. 1. More generally, master device 902 can be any type of device providing a master controller that can be physically manipulated by a user. Master device 902 generates control signals C1 to Cx indicating states or changes of one or more master controllers in their degrees of freedom. The master device 902 can also generate control signals (not shown) indicating selection of physical buttons and other manipulations by the user.

A control system 910 can be included in the master device 902, in the slave device 904, or in a separate device, e.g., an intermediary device, or can be distributed among multiple of these devices. Control system 910 receives control signals C1 to Cx and generates actuation signals A1 to Ay, which are sent to slave device 904. Control system 910 can also receive sensor signals B1 to By from the slave device 904 that indicate positions of various slave components (e.g., manipulator arm elements). Control system 910 can include general components such as a processor 912, memory 914, and interface hardware 916 and 918 for communication with master device 902 and slave device 904, respectively. Processor 912 can execute program code and control basic operations of the system 900, and can include one or more processors of various types, including microprocessors, application specific integrated circuits (ASICs), and other electronic circuits. Memory 914 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control system 910, e.g., display 920 such as the viewer 213 of the master control workstation 102 of FIG. 2.

In this example, control system 910 includes a user detection module 930, a mode control module 940, a controlling mode module 950, and a non-controlling mode module 960. As used herein, the term "module" refers to a combination of hardware (e.g., a processor such as an integrated circuit or other circuitry) and software (e.g., machine or processor executable instructions, commands, or code such as firmware, programming, or object code). A combination of hardware and software can include hardware only (i.e., a hardware element with no software elements), software hosted by hardware (e.g., software that is stored at a memory and executed or interpreted by or at a processor), or a combination of hardware and software hosted at hardware.

User detection module 930 can perform at least a portion of method 600 of FIG. 6. For example, user detection module 930 can control vibration on the master controller of the master device 902 as described herein, e.g., using one or more control signals D1 output to the actuator(s) used to apply vibration to the master controller as described herein. In some examples, control signals D1 can be actuator control signals used by the controlling mode module 950 (described below) to provide forces to the master controller during controlling mode, e.g., to provide force feedback, gravity compensation, etc. In some implementations, an actuator dedicated to the user detection described herein can be controlled by the user detection module 930 to provide vibration to the master controller.

The user detection module 930 can also receive sensor data from one or more of the control signals C1 to Cx indicating the positions or other characteristics of the master controller in response to the vibration, as described above. In some implementations, instead of using the control signals C1 to Cx, one or more sensor signals D2 dedicated to detecting the user touch can be received from one or more sensors of the master device, where sensor signals D2 describe the vibration sensed on the master controller.

Mode control module 940 can detect when a user initiates a controlling mode of the system, e.g., by user selection of controls, required manipulation of a master controller, etc. The mode control module 940 can also switch the mode of the master device automatically between controlling mode and non-controlling mode, for example, when user detection module 930 detects user touch, or a lack of user touch, on the master controller of the master device as described herein. In the controlling mode, control system 910 uses controlling mode module 950, which receives control signals C1 to Cx and generates actuation signals A1 to Ay that cause slave device 904 to follow the movement of master device 902. For example, mode control module 940 may activate controlling mode operation if user detection module 930 detects that a user is in proper position for use of the master control and that signals (e.g., one or more signals C1 to Cx or signals D2) indicate the user has contacted the master controller. The mode control module 940 may disable controlling mode if the user detection module 930 indicates that a user is not in proper position for use of the master controller and/or indicates that no user is touching the master controller.

Controlling mode module 950 may generate actuation signals A1 to Ay that cause slave device 904 to follow the movements of master device 902, e.g., so that the movements of slave 904 correspond to a mapping of the movements of master 902. Controlling mode module 950 can be implemented using conventional techniques. If no user touch is detected on the master controller, user detection module 930 may inform control module 910 to prevent the controlling mode module 950 from generating actuation signals A1 to An that move slave 904.

A non-controlling mode module 960 may be employed for a non-controlling mode of system 900. In the non-controlling mode, movement of one or more degrees of freedom of master 902 has no effect on the movement of one or more components of slave 904. In some examples, non-controlling mode may be used when a portion of slave 904, e.g., a slave arm assembly, is not being controlled by master 902, but rather is floating in space and may be manually moved. For non-controlling mode, non-controlling mode module 960 may allow actuator systems in the slave 904 to be freewheeling or may generate actuation signals A1 to An, for example, to allow motors in an arm to support the expected weight of the arm against gravity, where brakes in the arm are not engaged and permit manual movement of the arm. For example, in a medical procedure, non-controlling mode may allow a surgical side assistant to easily manipulate and reposition an arm or other slave component relative to a patient or directly make some other clinically appropriate adjustment of the arm or slave component.

Some implementations described herein, e.g., method 600, can be implemented, at least in part, by computer program instructions or code which can be executed on a computer. For example, the code can be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general purpose processors, graphics processors, Application Specific Integrated Circuits (ASICs), and the like.

Note that the functional blocks, operations, features, methods, devices, and systems described in the present disclosure may be integrated or divided into different combinations of systems, devices, and functional blocks as would be known to those skilled in the art.

Although the present implementations have been described in accordance with the examples shown, one of ordinary skill in the art will readily recognize that there can be variations to the implementations and those variations would be within the spirit and scope of the present disclosure. Accordingly, many modifications may be made by one of ordinary skill in the art without departing from the spirit and scope of the appended claims.

What is claimed is:

1. A method comprising:
controlling an actuator to cause a vibration in a handle of a control system, the handle manually moveable by a user, wherein the handle is provided with one or more degrees of freedom by one or more links coupled to the handle, wherein the one or more links are provided with one or more associated sensors of motion of the one or more links in the one or more degrees of freedom;
sensing the vibration with a sensor;
determining a vibration characteristic based on the sensing; and
determining a state of contact by the user with the handle based on the vibration characteristic,
wherein the one or more links are decoupled from the vibration such that the vibration in the handle is not sensed by the one or more associated sensors.

2. The method of claim 1, wherein determining the state of contact includes determining that a change in the vibration has occurred that satisfies one or more predetermined thresholds.

3. The method of claim 2, wherein the vibration is caused by applying a periodic control signal to the actuator, and wherein the change in the vibration includes a dampening of the vibration from a higher amplitude to a lower amplitude, wherein the lower amplitude is below one of the one or more predetermined thresholds.

4. The method of claim 1, further comprising controlling the actuator to modify the vibration after determining the state of contact by the user.

5. The method of claim 1, wherein the one or more links include a plurality of links rotatable about respective rotational axes, wherein the plurality of links are arranged in an orthogonal layout of successive rotational axes that decouples the vibration and the plurality of links.

6. The method of claim 1, wherein:
controlling the actuator causes the vibration in a degree of freedom of the handle;
determining the vibration characteristic based on the sensing includes determining a mean position of the handle in the degree of freedom during the vibration; and
determining the state of contact by the user with the handle includes determining a change in the mean position of the handle in the degree of freedom and comparing the change in the mean position to a mean position threshold.

7. The method of claim 1, wherein controlling the actuator to cause the vibration includes applying the vibration in a degree of freedom of the handle, and wherein the sensing the vibration with the sensor includes sensing the vibration in the degree of freedom of the handle.

8. The method of claim 1, further comprising sensing the user in physical proximity to the handle via a user presence sensor, wherein controlling the actuator to cause the vibration in the handle is initiated in response to sensing the user via the user presence sensor.

9. The method of claim 1, further comprising changing a frequency or an amplitude of the vibration in response to detecting a different operating mode of the control system, wherein the different operating mode includes at least one of: a camera control mode or a mode to control one or more functions of a device controlled by movement of the handle.

10. The method of claim 1, further comprising, in response to determining the state of contact, activating a controlling mode that includes controlling one or more actuators of a controlled device controlled by the control system to physically move at least a portion of the controlled device in correspondence with physical manipulation of the handle by the user.

11. The method of claim 1, wherein the vibration is a first vibration, and further comprising:
after determining the state of contact by the user, modifying the first vibration in the handle by controlling the actuator to apply a second vibration in the handle, wherein the second vibration has at least one of:
a different amplitude than the first vibration,
a different frequency than the first vibration, or
a combination of the different amplitude and the different frequency.

12. A system comprising:
a handle manually moveable by a user;
an actuator coupled to the handle;
a sensor of motion of the handle;
one or more links coupled to the handle, wherein the handle is provided with one or more degrees of freedom by the one or more links;
one or more associated sensors of motion of the one or more links in the one or more degrees of freedom;
a memory storing instructions; and
at least one processor coupled to the memory and to the actuator, the at least one processor configured to access the instructions in the memory and execute operations comprising:
controlling the actuator to cause a vibration in the handle;
sensing the vibration with the sensor;
determining a vibration characteristic based on the sensing; and
determining a state of contact by the user with the handle based on the vibration characteristic,
wherein the one or more links are decoupled from the vibration such that the vibration in the handle is not sensed by the one or more associated sensors.

13. The system of claim 12, wherein the operation of determining the state of contact includes determining that a change in the vibration has occurred that satisfies one or more predetermined thresholds.

14. The system of claim 12, wherein the operation of determining the vibration characteristic includes determining a mean position of the handle in a degree of freedom of the handle while the vibration is caused, and wherein determining the state of contact includes determining a change in the mean position of the handle in the degree of freedom and comparing the change in the mean position to a mean position threshold.

15. The system of claim 12, wherein the operations further comprise controlling the actuator to remove the vibration after determining the state of contact by the user.

16. The system of claim 12, wherein the one or more links include a plurality of links rotatable about respective rotational axes, wherein the plurality of links are arranged in an orthogonal layout of successive rotational axes that decouples the vibration and the plurality of links.

17. The system of claim 12, wherein the operation of controlling the actuator to cause the vibration includes applying the vibration in a degree of freedom of the handle, and wherein the sensing the vibration with the sensor includes sensing the vibration in the degree of freedom of the handle.

18. The system of claim 12, wherein the at least one processor is configured to execute operations further comprising:
sensing the user in physical proximity to the handle via a user presence sensor, wherein the operation of controlling the actuator to cause the vibration in the handle is initiated in response to sensing the user via the user presence sensor.

19. The system of claim 12, wherein the vibration is a first vibration, and wherein the at least one processor is configured to execute operations further comprising:
after determining the state of contact by the user, modifying the first vibration in the handle by controlling the actuator to apply a second vibration in the handle, wherein the second vibration has at least one of:
a different amplitude than the first vibration,
a different frequency than the first vibration, or
a combination of the different amplitude and the different frequency.

20. The system of claim 12, wherein the at least one processor is configured to execute operations further comprising:
in response to determining the state of contact, activating a controlling mode that includes controlling one or more actuators of a controlled device controlled by the system to physically move at least a portion of the controlled device in correspondence with physical manipulation of the handle by the user.

\* \* \* \* \*